United States Patent
Matsuyama et al.

(10) Patent No.: US 8,794,048 B2
(45) Date of Patent: Aug. 5, 2014

(54) SYSTEM FOR DETERMINING NUMBER OF PARTICLES

(75) Inventors: Takashi Matsuyama, Kyoto (JP); Masayoshi Shinohara, Kyoto (JP); Yoshinori Otsuki, Kyoto (JP); Kaoru Okada, Kyoto (JP); Masanobu Akita, Kyoto (JP)

(73) Assignee: Horiba, Ltd., Kyoto (JP)

( * ) Notice: Subject to any disclaimer, the term of this patent is extended or adjusted under 35 U.S.C. 154(b) by 251 days.

(21) Appl. No.: 13/259,018

(22) PCT Filed: Apr. 2, 2010

(86) PCT No.: PCT/JP2010/056090
§ 371 (c)(1),
(2), (4) Date: Sep. 22, 2011

(87) PCT Pub. No.: WO2010/116959
PCT Pub. Date: Oct. 14, 2010

(65) Prior Publication Data
US 2012/0090377 A1  Apr. 19, 2012

(30) Foreign Application Priority Data

Apr. 7, 2009 (JP) ................................ 2009-092915
Apr. 17, 2009 (JP) ................................ 2009-101359
Apr. 17, 2009 (JP) ................................ 2009-101443

(51) Int. Cl.
*G01N 7/00* (2006.01)
(52) U.S. Cl.
USPC ........................................................ 73/23.33
(58) Field of Classification Search
USPC ........................................................ 73/23.33
See application file for complete search history.

(56) References Cited

U.S. PATENT DOCUMENTS

| 4,823,591 | A | 4/1989 | Lewis | |
|---|---|---|---|---|
| 2006/0032217 | A1* | 2/2006 | Kondou et al. | 60/297 |
| 2006/0236752 | A1 | 10/2006 | Nakamura | |
| 2009/0308251 | A1* | 12/2009 | Kondou et al. | 96/19 |

FOREIGN PATENT DOCUMENTS

| JP | 51-077291 A | 7/1976 |
|---|---|---|
| JP | 55-065133 | 5/1980 |
| JP | 55-167554 U | 12/1980 |
| JP | 58-153550 | 9/1983 |
| JP | 59-082561 U | 6/1984 |
| JP | 59-130558 | 7/1984 |
| JP | 59-175157 U | 11/1984 |
| JP | 1989143932 A | 6/1989 |

(Continued)

*Primary Examiner* — Hezron E Williams
*Assistant Examiner* — David Z Huang
(74) *Attorney, Agent, or Firm* — Brooks Kushman P.C.

(57) ABSTRACT

A system for determining a number of particles includes a diluter arranged at a connecting point of a main flow channel and dilution gas flow channel, a dilution gas flow rate control part that controls the flow rate of the dilution gas introduced into the diluter, a particle number measuring unit that measures a number of solid particles in a diluted exhaust gas, a bypass flow channel that bifurcates from between the diluter and particle number measuring unit in the main flow channel and in which a constant flow rate unit is arranged, and an information processing unit that calculates the dilution factor of the exhaust gas based on a dilution gas flow rate controlled by the dilution gas flow rate control part, and a total of a unit flow rate of the particle number measuring unit and a set flow rate of the constant flow rate unit.

5 Claims, 12 Drawing Sheets

(56) References Cited

FOREIGN PATENT DOCUMENTS

| | | |
|---|---|---|
| JP | 06-341950 | 12/1994 |
| JP | 2000028499 A | 1/2000 |
| JP | 2001188031 A | 7/2001 |
| JP | 2001-215230 | 8/2001 |
| JP | 2002-536634 A | 10/2002 |
| JP | 2003-307470 | 10/2003 |
| JP | 2006-077761 | 3/2006 |
| JP | 2006-194744 | 7/2006 |
| JP | 2006194726 A | 7/2006 |
| JP | 2006275801 A | 10/2006 |
| JP | 2008-096182 | 4/2008 |
| JP | 2008164413 A | 7/2008 |
| JP | 2008164419 A | 7/2008 |
| JP | 2008164446 A | 7/2008 |
| JP | 2008530558 A | 8/2008 |
| JP | 2009-008525 | 1/2009 |
| JP | 2009510448 A | 3/2009 |
| JP | 2010-515017 A | 5/2010 |
| JP | 2010-515018 A | 5/2010 |
| WO | 00-46584 | 8/2000 |
| WO | 2006086615 A2 | 8/2006 |
| WO | 2007041274 A2 | 4/2007 |
| WO | 2008-079845 A | 7/2008 |
| WO | 2008-079863 A2 | 7/2008 |

* cited by examiner

SYSTEM FOR DETERMINING NUMBER OF PARTICLES

FIELD OF THE ART

This invention relates to a system for determining number of particles that measures a number of solid particles such as particulate matters (PM) contained in en exhaust gas of an engine.

BACKGROUND ART

As a method for measuring particulate matters (PM) as being one of exhausted materials from an engine well known is a filter mass method that collects particulate matters by the use of a filter and measures a mass of the particulate matters. However, since the exhausted amount of the particulate matters has been subtle, it becomes difficult for the filter mass method to measure the amount in view of the accuracy. Under this condition, as its alternative method developed is a method for measuring a number of the particulate matters in the exhaust gas. A concrete system structure is known that a diluter to dilute the exhaust gas of the engine with air or the like is arranged upstream of a particle number measuring unit, and a part of the diluted exhaust gas is introduced into the particle number measuring unit and then the number of the particles contained in the diluted exhaust gas is counted (refer to the patent document 1).

Conventionally, the dilution unit of this system comprises a diluter arranged at a connecting point of the main flow channel where the exhaust gas flows and the dilution gas flow channel where the dilution gas flows or near downstream of the connecting point, a flow rate measuring mechanism to measure a mss flow rate of the exhaust gas introduced into the diluter, a dilution gas flow rate control part to control the mass flow rate of the dilution gas introduced into the diluter and an exhaust gas flow rate control part to change the mass flow rate of the exhaust gas. Then a desired dilution factor is realized by measuring the flow rate of the exhaust gas flowing into the dilution unit by means of the flow rate measuring mechanism and by controlling the flow rate of the exhaust gas by means of the exhaust gas flow rate control part.

The flow rate control mechanism comprises an orifice part as being a fluid resistance, a pressure sensor that measures a differential pressure of the orifice part, and a pressure sensor that measures an absolute pressure in the upstream side, and is so arranged that an information processing unit, separately arranged, calculates a mass flow rate of the exhaust gas introduced into the diluter based on the pressure information upstream and downstream of the orifice part.

However, if the orifice part, the pressure sensor for measuring the differential pressure, the pressure sensor for measuring the absolute pressure and a temperature adjustor are arranged in the upstream side of the diluter, there are not only a problem that the system for determining the number of particles becomes bulky but also a problem that a number of components increases so as to increase its cost.

In addition, the system for determining the number of particles has an arrangement that a bypass flow channel is arranged between the dilution unit and the particle number measuring unit, air whose flow is controlled by a mass flow controller is supplied to the bypass flow channel and the flow rate of the exhaust gas introduced into the particle number measuring unit from the dilution unit is adjusted.

However, since this arrangement uses the mass flow controller, there are problems such that not only the system for determining a number of particles becomes bulky but also its cost increases.

PRIOR ART DOCUMENT

Patent Document

Patent document 1: Japanese Unexamined Patent Application Publication No. 2006-194726
Patent document 2: Japanese Unexamined Patent Application Publication No. 2008-164446

DISCLOSURE OF THE INVENTION

Problems to be Solved by the Invention

The present claimed invention intends to solve all of the above-mentioned problems, and its main object is to simplify and downsize a structure of the system for determining a number of particles and to reduce its cost.

Means to Solve the Problems

The system for determining a number of particles is characterized by comprising an exhaust gas introduction port to introduce an exhaust gas of an engine, a dilution gas introduction port to introduce a dilution gas, a main flow channel whose one end is connected to the exhaust gas introduction port, a dilution gas flow channel whose one is connected to the dilution gas introduction port and whose other end is connected to the main flow channel, a diluter arranged at a connecting point of the main flow channel and the dilution gas flow channel or near downstream of the connecting point, a dilution gas flow rate control part that is arranged in the dilution gas flow channel and that controls a flow rate of the dilution gas introduced into the diluter, a particle number measuring unit, having a function of a constant flow rate, that is arranged downstream of the diluter through a valve and that measures a number of solid particles in the diluted exhaust gas, a bypass flow channel that bifurcates from between the diluter and the particle number measuring unit in the main flow channel and in which a constant flow rate unit and a valve are arranged, a suction pump that is connected to downstream of a converging point of the main flow channel and the bypass flow channel and that is to introduce the exhaust gas into the main flow channel and the bypass flow channel, and an information processing unit that calculates a dilution factor of the exhaust gas based on the dilution gas flow rate controlled by the dilution gas flow rate control part and a total of a unit flow rate as being a flow rate flowing in the particle number measuring unit and a set flow rate of the constant flow rate unit in the bypass flow channel.

In accordance with this arrangement, since the dilution factor is calculated based on the dilution gas flow rate controlled by the dilution gas flow rate control part and a total of the unit flow rate of the particle number measuring unit and the set flow rate of the constant flow rate unit in the bypass flow channel, it is possible to omit a flow rate measuring mechanism that measures a flow rate of an exhaust gas flowing in a conventional dilution unit. As a result, it is possible to simplify and downsize the system configuration, and to decrease its cost as well. In addition, since a suction pump conventionally provided for the flow channel where the particle number measuring unit and a suction pump conventionally provided for the bypass flow channel can be commonly used, it is possible to simplify and downsize the configuration of the system, and to reduce its cost.

There is a case that a flow rate shown by the constant flow rate unit in the bypass flow channel differs from a set flow rate in a state (an initial state) that the constant flow rate unit is incorporated into the system. In order to prevent a fluctuation of the dilution factor, it is preferable that the information processing unit corrects the set flow rate of the constant flow rate unit in the bypass flow channel by closing the valve arranged upstream of the particle number measuring unit and by opening the valve arranged in the bypass flow channel so as to flow a flow rate controlled by the dilution gas flow rate control part into the bypass flow channel.

Similar to the same reason, it is preferable that the information processing unit corrects the unit flow rate of the particle number measuring unit in the bypass flow channel by closing the valve arranged in the bypass flow channel and by opening the valve arranged upstream of the particle number measuring unit so as to flow a flow rate controlled by the dilution gas flow rate control part into the main flow channel.

Even though the set flow rate of the constant flow rate unit is corrected as mentioned above, the temperature and the pressure in the flow channel at a time of correction differ from the temperature and the pressure in the flow channel at a time of measuring the number of particles. Then the flow rate flowing in the constant flow rate unit fluctuates. In order to solve this problem, it is preferable that the information processing unit corrects the set flow rate of the constant flow rate unit in the bypass flow channel by making use of a temperature and a pressure near upstream of the constant flow rate unit at a time of correcting the constant flow rate unit in the bypass flow channel and a temperature and a pressure near upstream of the constant flow rate unit in the bypass flow channel at a time of measuring the number of the particles as a parameter.

Similar to the same reason, it is preferable that the information processing unit corrects the unit flow rate of the particle number measuring unit by making use of a pressure near upstream of the particle number measuring unit at a time of correcting the unit flow rate of the particle number measuring unit and a pressure near upstream of the particle number measuring unit at a time of measuring the number of the particles as a parameter.

Effect of the Invention

In accordance with the invention having the arrangement, it is possible to simplify and downsize a structure of the system for determining a number of particles and to reduce its cost.

EXPLANATION OF CODES

Figure 1:
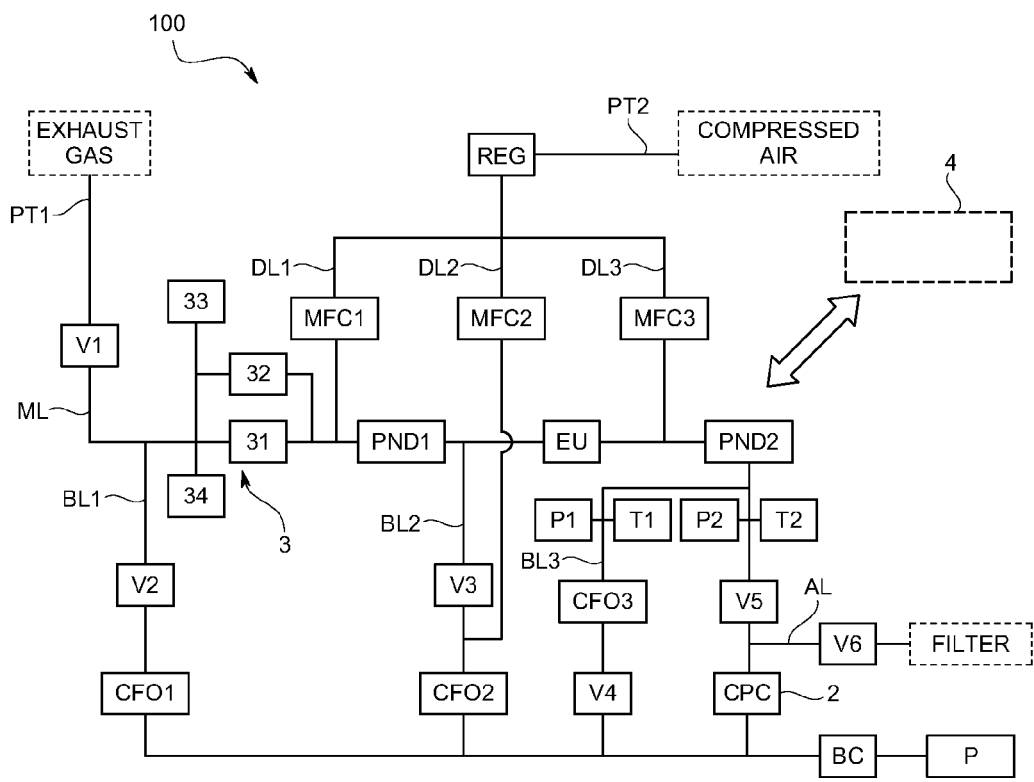
FIG. 1 is a whole configuration diagram of a system for determining a number of particles in accordance with one embodiment of this invention.

100 . . . system for determining number of particles
PT1 . . . exhaust gas introduction port
PT2 . . . dilution gas introduction port
ML . . . main flow channel
DL . . . dilution gas flow channel
PND . . . diluter
MFC . . . dilution gas flow rate control part
V5 . . . valve
2 . . . particle number measuring unit
CFO3 . . . constant flow rate unit
V4 . . . valve
BL . . . bypass flow channel
P . . . suction pump
4 . . . information processing unit

BEST MODES OF EMBODYING THE INVENTION

One embodiment of a system for determining a number of particles in accordance with this invention will be explained with reference to drawings.

The system for determining the number of particles (100) in accordance with this embodiment introduces an exhaust gas of an engine into a main flow channel (ML) arranged inside through an exhaust gas introduction port (PT1), dilutes or evaporates the introduced exhaust gas, and measures particulate matters (PM) as being solid particles in the exhaust gas by means of a particle number measuring unit (2) arranged in the main flow channel (ML).

The exhaust gas introduction port (PT1) is connected to an exhaust gas line from an engine, not shown in drawings, and is so arranged to introduce, for example, the exhaust gas directly from the engine or the exhaust gas diluted by a whole flow dilution tunnel or a diverted flow dilution tunnel into the exhaust gas introduction port (PT1). The exhaust gas hereinafter called as the exhaust gas includes the diluted exhaust gas as mentioned above.

A part of the exhaust gas introduced into the inside through an open/close valve (V1) from the exhaust gas introduction port (PT1) is discharged from the first bypass flow channel (BL1) and the remaining exhaust gas is introduced into the serially arranged multiple (two, in this embodiment) diluters (PND1, PND2) and then diluted with air as being the dilution gas.

The air is supplied to each part of the main flow channel (ML) or the second bypass flow channel (BL2) after passing the multiple dilution gas flow channels (DL1~DL3) from the dilution gas introduction port (PT2) through a regulator (REG).

In addition, the first bypass flow channel (BL1) converges on the main flow channel (ML) in the downstream of the particle number measuring unit (2), to be described later, and the open/close valve (V2) and a constant flow rate unit (CFO1) such as a critical orifice that keeps a flow rate flowing in the bypass flow channel (BL1) at a constant value are arranged in this order in the first bypass flow channel (BL1). Furthermore, a suction pump (P) to make the main flow channel (ML) and the bypass flow channels (BL1~BL3) at a negative pressure is connected to a downstream of a converged point of the main flow channel (ML) and the bypass flow channels (in addition to the first bypass flow channel BL1, the other bypass flow channels (BL2~BL3), to be described later, are included). In addition, a buffer chamber (BC) to smooth a fluctuation of a sucking force of the suction pump (P) is arranged near an upstream side of the suction pump (P).

The primary diluter (the diluter locating in the upstream side) (PND1) is arranged at a connecting point of the main flow channel (ML) and the dilution gas flow channel (DL) or near the downstream of the connecting point, and applies heat to the exhaust gas introduced into the primary diluter (PND1) and dilutes the heated exhaust gas.

A mass flow rate of the exhaust gas as being the diluted gas to be introduced into the primary diluter (PND1) is measured by a flow rate measuring mechanism (3) arranged on the upstream of the primary diluter (PND1), more concretely on the upstream of the connecting point.

Figure 2:
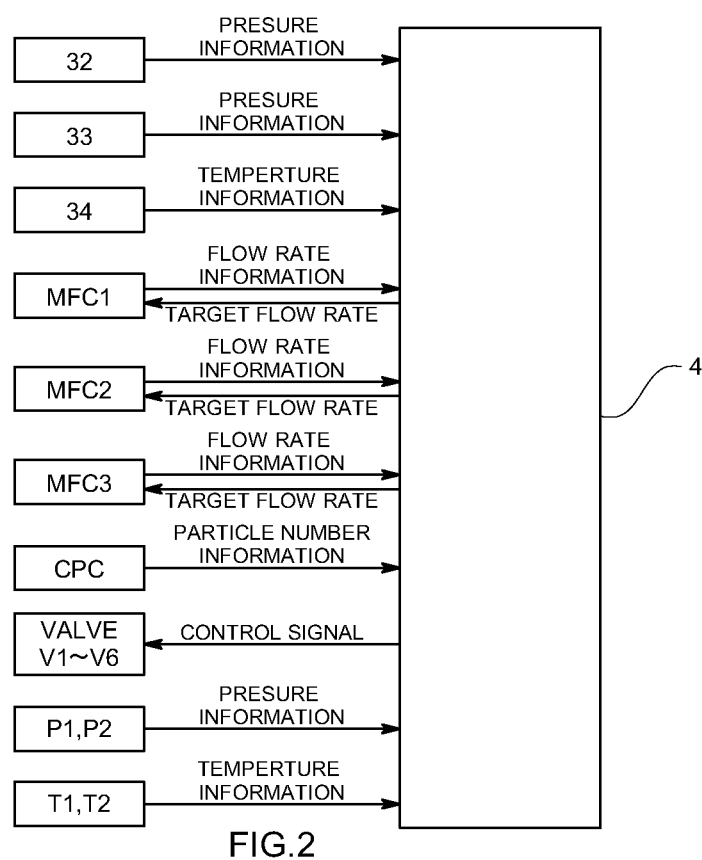
FIG. 2 is an information transmitting diagram showing a flow of information in accordance with this embodiment.

The flow rate measuring mechanism (3) comprises an orifice part 31 as being a fluid resistance, a pressure sensor (32) that measures a differential pressure of the orifice part (31), a pressure sensor (33) that measures an absolute pressure in the upstream side and a temperature adjustor (34) that adjusts a temperature of the fluid, and the separately arranged information processing unit (4), (especially, refer to FIG. 2) calculates the mass flow rate of the exhaust gas introduced into the primary diluter (PND1) based on the pressure information in the upstream and downstream of the orifice part (31) and the temperature information from the temperature adjustor (34). The information processing unit 4 comprises a CPU, a memory, an input/output device and a display, and is a so-called general purpose or dedicated computer operating in cooperation with the CPU and its peripheral devices based on predetermined programs stored in the memory.

In addition, the mass flow rate of the dilution gas introduced into the primary diluter (PND1) is controlled by the dilution gas flow rate control part (MFC1) arranged in the dilution gas flow channel (DL1). The dilution gas flow rate control part (MFC1) controls the flow rate locally by adjusting the valve (not shown in drawings) of the inside so that the actual flow rate measured by the flow rate sensor (not shown in drawings) arranged inside becomes a value of a target flow rate data (hereinafter also called as a target flow rate) in case that the target flow rate data is given by the information processing unit (4). The target flow rate is calculated by the information processing unit (4) based on the dilution factor.

Furthermore, an evaporator (EU) to evaporate volatile particles is arranged in the downstream of the primary diluter (PND1), and a second bypass flow channel (BL2) that converges on the main flow channel (ML) in the downstream of the particle number measuring unit (2) is arranged to bifurcate from between the primary diluter (PND1) and the evaporator (EU). The evaporator (EU) is heated at 300~400 degrees.

A dilution gas flow channel (DL2) where the dilution gas flow rate control part (MFC2) is arranged is connected to the second bypass flow channel (BL2). An open/close valve (V3) and a constant flow rate unit (CFO2) such as a critical orifice that keeps a flow rate flowing in the second bypass flow channel (BL2) at a constant value are arranged in the second bypass flow channel (BL2). With this arrangement, the dilution gas flow rate control part (MFC2) is controlled by the information processing unit (4) so that the dilution gas flowing into the second bypass flow channel (BL2) is adjusted. As a result of this, the mass flow rate of the exhaust gas flowing into the second bypass flow channel (BL2) from the main flow channel (ML) is adjusted.

The secondary diluter (the diluter in the downstream side) (PND2) is arranged at a connecting point of the main flow channel (ML) and the dilution gas flow channel ((DL3) or neat the connecting point in the downstream, and cools down the exhaust gas introduced into the secondary diluter (PND2) and dilutes the exhaust gas.

A mass flow rate of the exhaust gas introduced into the secondary diluter (PND2) is controlled by a dilution gas flow rate control part (MFC3) arranged in the dilution gas flow channel (DL3). Similar to the dilution gas flow rate control part (MFC1), the dilution gas flow rate control part (MFC3) controls the flow rate locally by adjusting the valve of the inside (not shown in drawings) so that the actual flow rate measured by the flow rate sensor (not shown in drawings) arranged inside becomes a value of a target flow rate data (hereinafter also called as a target flow rate) in case that the target flow rate data is given by the information processing unit (4). The target flow rate is calculated by the information processing unit (4) based on the dilution factor.

With this arrangement, a pipe from the primary diluter (PND1) and its vicinity to the secondary diluter (PND2) is heated at, for example, 150 degrees and over by a temperature adjustor having a heating means such as a heater or the like, not shown in drawings. This arrangement prevents the particulate matters (PM) from attaching or agglutinating to an inside wall of the pipe so that an error in measuring the number of the particulate matters can be prevented.

In addition, the particle number measuring unit (2) that measures the number of solid particles in the exhaust gas diluted by the primary diluter (PND1) and the secondary diluter (PND2) is arranged through an open/close valve (V5) in the downstream of the secondary diluter (PND2), and a third bypass flow channel (BL3) that converges on the main flow channel (ML) is arranged between the secondary diluter (PND2) and the particle number measuring unit (2), concretely the third bypass flow channel (BL3) bifurcates from the upstream of the open/close valve (V5) and converges on the main flow channel (ML) in the downstream of the particle number measuring unit 2.

A constant flow rate unit (CFO3) such as a critical orifice that keeps a flow rate flowing in the bypass flow channel (BL3) at a constant value and the open/close valve (V4) are arranged in this order in the third bypass flow channel (BL3). An atmosphere releasing path (AL) where an open/close valve (V6) and a filter are arranged in this order is formed between the open/close valve (V5) and the particle number measuring unit (2), and the atmosphere releasing path (AL) releases the atmosphere in the particle number measuring unit (2) by opening the open/close valve (V6) in case of closing the open/close valve (V5) at a time when the suction pump (P) is halted or the like.

The particle number measuring unit (2) grows the particulate matters to be in a big diameter by mixing in an organic gas such as alcohol or butanol in a supersaturated state and attaching the organic gas to the particulate matters in the exhaust gas and discharges the grown particulate matters from a slit so as to measure a number of the particulate matters by irradiating the laser light on the discharged particulate matters. Since the particle number measuring unit (2) is so arranged to discharge the grown particulate matters from the slit, the slit serves as a function of a constant flow rate unit so that a constant flow rate of the exhaust gas flows in the particle number measuring unit (2).

In accordance with this arrangement, a part of the exhaust gas diluted by the two diluters (PND1) and (PND2) is introduced into the particle number measuring unit (2) and a number of solid particles contained in the exhaust gas is counted. Then the counted data measured by the particle number measuring unit (2) is output to the information processing unit (4) and appropriately processed.

The information processing unit (4) of this embodiment calculates the dilution factor of the exhaust gas based on the dilution gas flow rate ($Q_1$) controlled by the dilution gas flow rate control part (MFC3), and the total flow rate ($Q_2+Q_3$) of the unit flow rate ($Q_2$) as being the flow rate flowing in the particle number measuring unit (2) and the set flow rate ($Q_3$) of the constant flow rate unit (CFO3) in the third bypass flow channel (BL3). Concretely, the information processing unit (4) calculates the dilution factor by $(Q_2+Q_3)/(Q_2+Q_3-Q_1)$. This arrangement contributes to omitting a flow rate measuring mechanism that measures a mass flow rate of the exhaust gas introduced into the secondary diluter (PND2).

In addition, the information processing unit (4) of this embodiment corrects the set flow rate of the constant flow rate unit (CFO3) in the third bypass flow channel (BL3) by closing the open/close valve (V5) arranged upstream of the particle number measuring unit (2) and by opening the open/close valve (V4) arranged in the third bypass flow channel (BL3) so as to flow a flow rate ($Q_1$) controlled by the dilution gas flow rate control part (MFC3) into the third bypass flow channel (BL3). A pressure and a temperature near upstream of the constant flow rate unit (CDO3) at a time of correction are measured by a pressure sensor (P1) and a temperature sensor (T1) and the information processing unit (4) stores the measurement data in association with the correction data.

Meanwhile, the information processing unit (4) corrects the unit flow rate of the particle number measuring unit (2) by closing the open/close valve (V4) arranged in the third bypass flow channel (BL3) and by opening the open/close valve (V5) arranged upstream of the particle number measuring unit (2) so as to flow the flow rate ($Q_1$) controlled by the dilution gas flow rate control part (MFC3) into the main flow channel (ML). A pressure and a temperature near upstream of the particle number measuring unit (2) at a time of correction are measured by a pressure sensor (P2) and a temperature sensor (T2) and the information processing unit (4) stores the measurement data in association with the correction data.

Furthermore, the information processing unit (4) of this embodiment corrects the set flow rate (a set flow rate after collection ($Q_3'$)) of the constant flow rate unit (CFO3) in the third bypass flow channel (BL3) by making use of a temperature and a pressure near upstream of the constant flow rate unit (CFO3) at a time of correcting the constant flow rate unit (CFO3) in the third bypass flow channel (BL3) and a temperature and a pressure near upstream of the constant flow rate unit (CFO3) in the third bypass flow channel (BL3) at a time of measuring the number of the particles as a parameter. Furthermore, the information processing unit (4) corrects the unit flow rate (a unit flow rate after collection ($Q_2'$)) of the particle number measuring unit (2) by making use of a temperature and a pressure near upstream of the particle number measuring unit (2) at a time of correcting the unit flow rate of the particle number measuring unit (2) and a temperature and a pressure near upstream of the particle number measuring unit (2) at a time of measuring the number of the particles as a parameter. Then the information processing unit (4) calculates the dilution factor by the use of the unit flow rate ($Q_2'$) and the set flow rate ($Q_3'$) obtained as a result of correction and gives a target flow rate data to the dilution gas flow rate control part (MFC3) so as to make the dilution factor of the secondary diluter (PND2) at a constant value.

Next, the diluter (PND) of this embodiment will be explained.

The system for determining the number of particles in accordance with this embodiment comprises a main flow channel whose one end is connected to an exhaust gas introduction port to introduce an exhaust gas of an engine, a dilution gas flow channel whose one end is connected to a dilution gas introduction port to introduce a dilution gas and whose other end is connected to the main flow channel, an evaporator that is arranged in the main flow channel and that evaporates volatile particles in the exhaust gas, a downstream side diluter that is arranged in a downstream side of the evaporator and that dilutes the exhaust gas by mixing the dilution gas into the exhaust gas passing the evaporator and a particle number measuring unit that measures a number of solid particles in the exhaust gas diluted by the downstream side diluter. The downstream side diluter comprises a body having an internal space in a shape of a body of revolution whose diameter diminishes from one end to the other end, an introducing pipe that is arranged along a center axial line of the internal space or orthogonal to the center axial line and that introduces the exhaust gas and the dilution gas into the internal space, and a lead-out pipe that is arranged orthogonal to the introducing pipe and that leads out the exhaust gas diluted by a swirling flow generating inside of the internal space to outside of the internal space. The body is so arranged that the center axial line of the internal space is generally horizontal, the introducing pipe is connected to the evaporator, and the lead-out pipe is connected to the particle number measuring unit.

In accordance with this arrangement, since the downstream side diluter has the introducing pipe and the lead-out pipe each of which is orthogonal and the lead-out pipe leads out the exhausted gas diluted by the swirling flow in the internal space of the body, it is possible to fully mix the exhaust gas and the dilution gas by the downstream side diluter and to change a direction of the flow channel. As a result, it is possible to make it unnecessary a cubic volume occupied by the bent pipe due to a bend radius based on a conventional flow rate and to convert a direction of the flow channel with a compact arrangement. Especially, since the center axis of the internal space of the downstream side diluter is arranged generally horizontally, it is possible to send the diluted exhaust gas to the particle number measuring unit in a state that the pipe from the downstream side diluter to the particle number measuring unit is straight without accumulation of particles inside of the pipe. In addition, with a structure wherein a downstream side diluter is not provided in a vertical down side of the particle number measuring unit whose capacity and weight is big, it is possible to prevent a complicated structure of the system as a whole. Furthermore, since the downstream side diluter and its downstream are at a normal temperature without any structure to heat the exhaust gas and the pipe, it is conceivable that the particles attach to inside of the pipe because of the temperature drop. However, since the pipe can be shortened, it is possible to prevent the particles from attaching to the pipe. In addition, since the exhaust gas and the dilution gas are made to be the swirling flow in the internal space, it is possible to elongate a length of the flow channel where the exhaust gas and the dilution gas are mixed. Furthermore, since the exhaust gas and the dilution gas flowing back form the other end to one end due to the swirling flow are lead out to the outside from the lead-out port, it is possible to mix the exhaust gas and the dilution gas sufficiently without elongating the pipe.

In order to prevent particle loss in the introducing pipe and the lead-out pipe even though the introducing pipe and the lead-out pipe of the downstream side diluter are of a straight pipe respectively, it is preferable that a connecting part of the evaporator to the introducing pipe is arranged to be orthogonal to a connecting part of the particle number measuring unit to the lead-out pipe.

In order to further downsize the system for determining the number of particles as a whole, it is preferable that the system further comprises an upstream side diluter that is arranged upstream side of the evaporator and that dilutes the exhaust gas by mixing the dilution gas with the exhaust gas introduced into inside, and the upstream side diluter has a body having an internal space in a shape of a body of revolution whose diameter diminishes from one end to the other end, an introducing pipe that is arranged along a center axial line of the internal space or orthogonal to the center axial line and that introduces the exhaust gas and the dilution gas into the internal space, and a lead-out pipe that is arranged orthogonal to the introducing pipe and that leads out the exhaust gas diluted by a swirling flow generating inside of the internal space to outside of the internal space, and the upstream side diluter is heated, the downstream side diluter is cooled down, and a mounting flat surface on which a heater is mounted is formed on an outer wall of the body of the upstream side diluter.

In addition, since the exhaust gas in the upstream side diluter might contain foreign materials other than an object material to be measured or solid particles whose diameter is bigger than a predetermined diameter, in order to remove the foreign materials or the solid particles whose diameter is bigger than the predetermined diameter, it is preferable that the internal space is in a shape of a body of revolution whose diameter gradually diminishes toward a vertically downward, and a dust collecting part is arranged on the lower side of the internal space. At this time, it is preferable that the upstream side diluter comprises a function of removing foreign materials or solid particles whose size is bigger than the object material to be measured.

Figure 3:
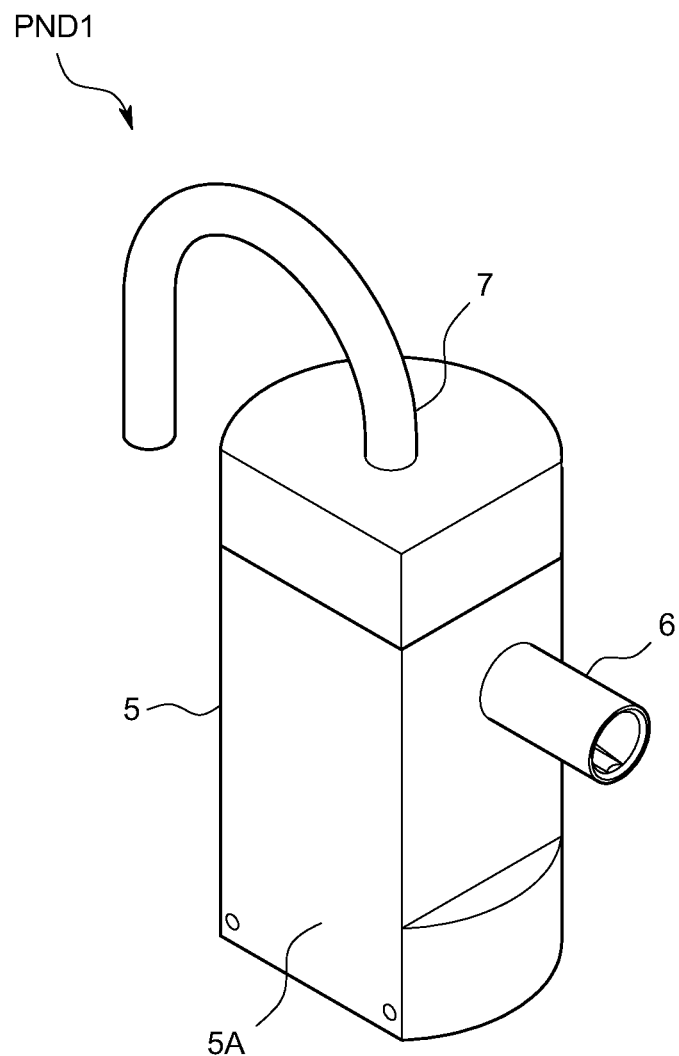
FIG. 3 is a perspective view of a primary diluter of this embodiment.
Figure 4:
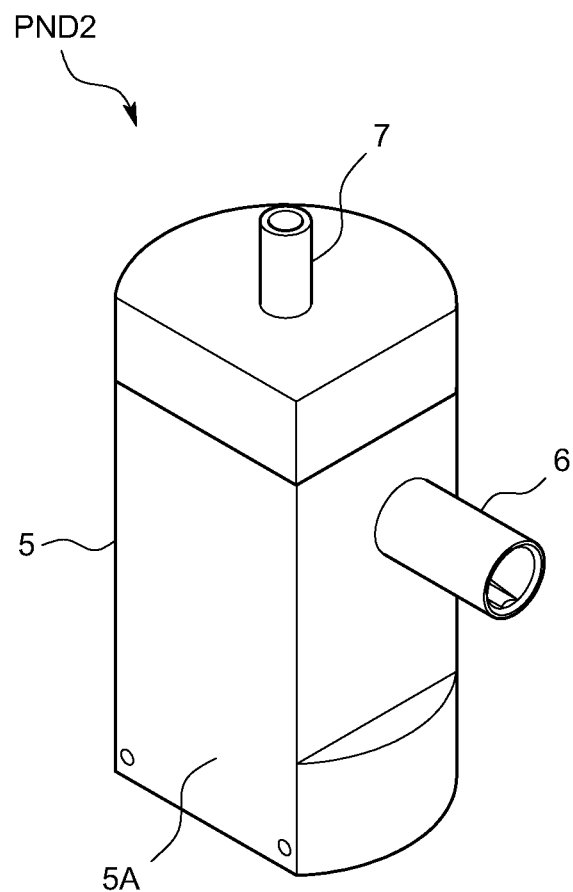
FIG. 4 is a perspective view of a secondary diluter of this embodiment.

The primary diluter (PND1) and the secondary diluter (PND2) of this embodiment comprise, as shown in FIG. 3 and FIG. 4, the body (5) having the internal space (S) into which the exhaust gas and the dilution gas are introduced, the introducing pipe (6) that introduces the exhaust gas and the dilution gas into the internal space (S) of the body (5), and the lead-out pipe (7) that leads out the diluted exhaust gas from the internal space (S). FIG. 3 shows the primary diluter (PND1), FIG. 4 shows the secondary diluter (PND2), and the structure of the primary diluter (PND 1) and the structure of the secondary diluter (PND2) are the same except for the lead-out pipe (7).

For the body (5) formed is the internal space (S) in a shape of a body of revolution having a tapered part whose diameter diminishes from one end to the other end. Concretely, the internal space (S) comprises a cylindrical space part (S1) and a conical space part (S2). At the other end part of the internal space (S) arranged is a dust catching part (8) to be connected to the internal space (S) so as to collect dusts contained in the exhaust gas introduced into the internal space (S).

In addition, in case of being used for the primary diluter (PND1), a flat surface (5A) for mounting a heater to heat the exhaust gas introduced into the internal space (S) is formed on an outer wall of the body (5).

Figure 6:
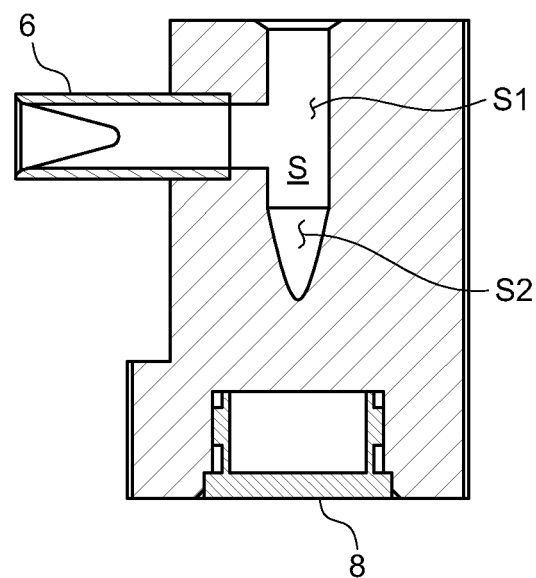
FIG. 6 is a longitudinal cross sectional view taken along a center axis of an introducing pipe of the diluter in accordance with this embodiment.
Figure 7:
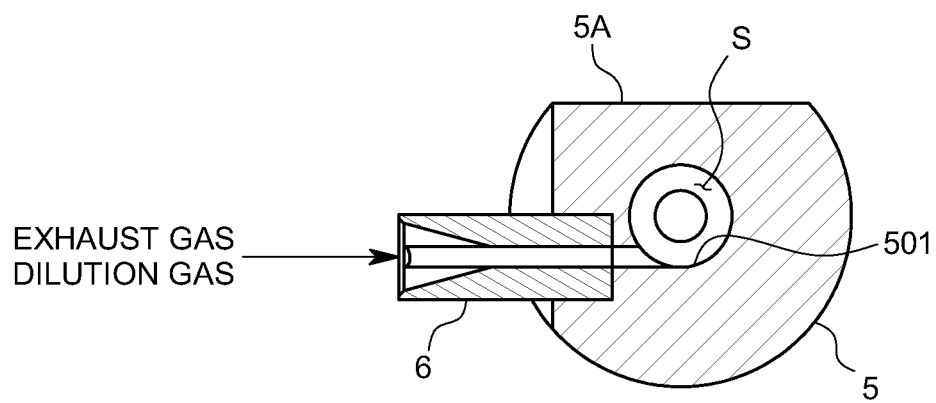
FIG. 7 is a transversal cross sectional view taken along a center axis of the introducing pipe of the diluter in accordance with this embodiment.

The introducing pipe (6) introduces the exhaust gas and the dilution gas into the internal space (S) from each cylindrical part of the diluters (PND1), (PND2) so as to make the exhaust gas and dilution gas to be the swirling flow heading downward (the other end) along the internal wall of the body (5). Concretely the introducing pipe (6) is arranged, as shown in FIG. 6, orthogonal to a center axis (C) of the internal space (S) in the cylindrical space part (S1) locating above the tapered part (the conical space part (S2)) in the internal space (S), and furthermore, as shown in FIG. 7, the introducing pipe (6) is arranged at a position so as to make a flowing direction of the exhaust gas and the dilution gas in the tangential direction to a cylindrical wall (501) as being the internal wall of the body (5). The exhaust gas and the dilution gas flowing in from the introduction pipe (6) change from a straight flow to a swirling flow in the cylindrical space part (S1), and head downward (the other end) with whirling along the cylindrical wall (501), and when the exhaust gas and the dilution gas reach the conical space part (S2), the exhaust gas and the dilution gas increase its rotation speed and head further downward (the other end), and then change its direction near the bottom end of the conical space part (S2) and head upward with rotating around the center part and are finally discharged through the lead-out pipe (7).

Figure 5:
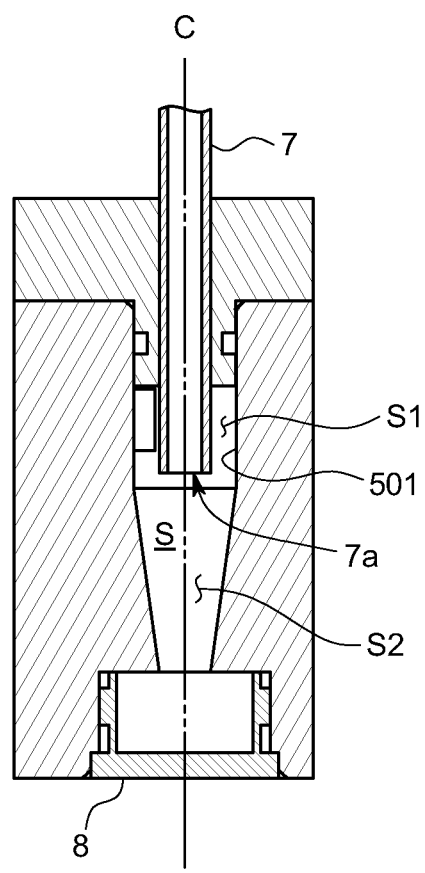
FIG. 5 is a longitudinal cross sectional view taken along a center axis of an internal space of the diluter in accordance with this embodiment.

The lead-out pipe (7) is arranged, as shown in FIG. 5, along the center axis (C) of the internal space (S) at least in the internal space (S), and its lead-out port (7a) is arranged in the internal space (S) (concretely, in the cylindrical space part (S1)), and leads out the exhaust gas diluted by the swirling flow generating in the internal space (S) to outside of the internal space (S). In other words, the lead-out pipe (7) and the introducing pipe (6) in the internal space (S) are arranged orthogonally each other. With this arrangement, it is possible to change the direction of the flow channel of the pipe constituting the main flow channel (ML) of the diluters (PND1) and (PND2). Furthermore, the lead-out port (7a) of the lead-out pipe (7) locates downward of the opening of the introducing pipe (6) so that the exhaust gas and the dilution gas never flow from the introducing pipe (6) directly to the lead-out pipe (7).

In addition, in this embodiment, the lead-out pipe (7) of the primary diluter (PND1) is, as shown in FIG. 3, a curved pipe that curves outside of the internal space (S) and the lead-out pipe (7) of the secondary diluter (PND2) is, as shown in FIG. 4, a straight pipe outside of the internal space (S).

In accordance with the diluters (PND1) and (PND2) having the above-mentioned arrangement, the primary diluter (PND1) is so arranged that the diameter of its internal space (S) gradually diminishes along a vertical downward direction. In other words, the primary diluter (PND1) is so arranged that the center axis (C) of its internal space (S) is generally vertical. With this arrangement, the dust contained in the exhaust gas introduced into the primary diluter (PND1) is centrifugalized and collected by the dust catching part (8). The primary diluter (PND1) has a function of removing particles whose diameter is bigger (for example, bigger than 2.5 μm) than that of the solid particles contained in the exhaust gas. Meanwhile, the secondary diluter (PND2) is so arranged that the center axis (C) of its internal space (S) is generally horizontal. In other words, the secondary diluter (PND2) does not have a function of collecting dusts.

Figure 8:
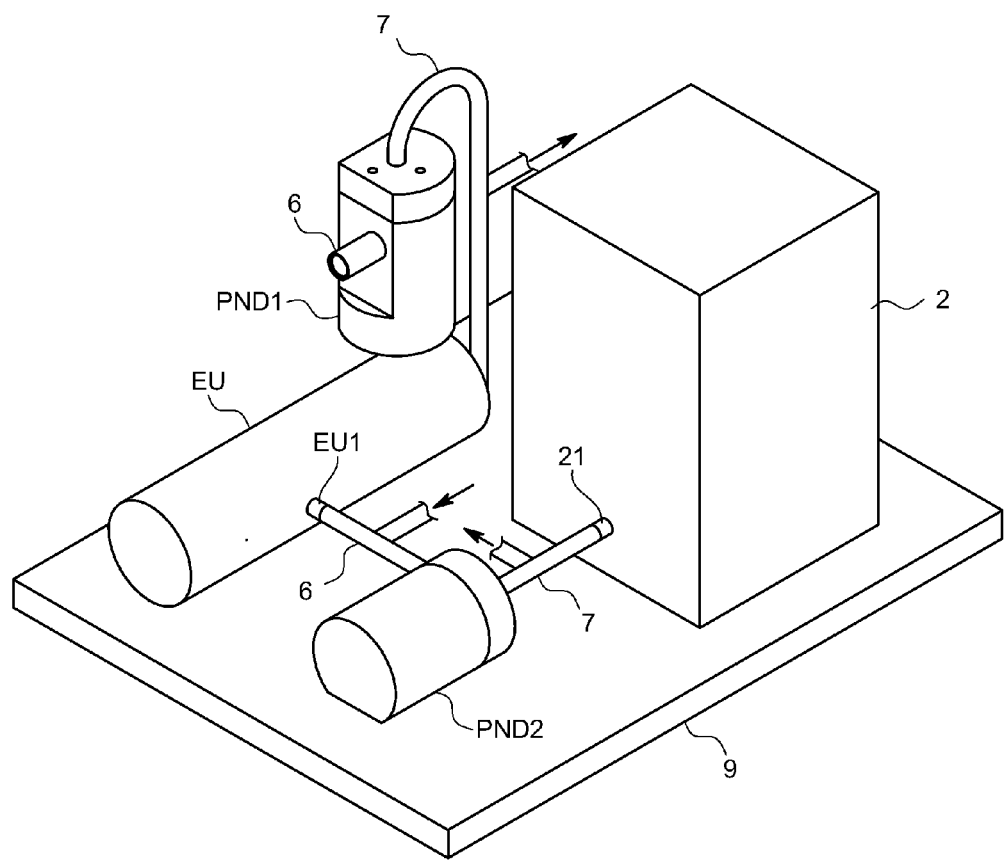
FIG. 8 is a pattern perspective view showing a layout of the primary diluter, the secondary diluter, an evaporator and a particle number measuring unit of this embodiment.

Next, a layout of the primary diluter (PND1), the secondary diluter (PND2), the evaporator (EU) and the particle number measuring unit (2) will be explained with reference to FIG. 8. The primary diluter (PND1) is arranged above the evaporator (EU) with the center axis (C) of its internal space (S) generally vertical, and the lead-out pipe (7) of the primary diluter (PND1) is curved in a channel shape. Then the lead-out pipe (7) is connected to one end of the evaporator (EU) arranged below. In addition, the introducing pipe (6) of the secondary diluter (PND2) is connected to an introducing pipe connecting part (an exhaust gas lead-out port) (EU1) of the evaporator (EU). The secondary diluter (PND2) is so arranged that the center axis (C) of its internal space (S) becomes generally horizontal, and the lead-out pipe (7) of the secondary diluter (PND2) is of a straight pipe and connected to the lead-out pipe connecting part (the exhaust gas introduction port) (21) of the particle number measuring unit (2). The introducing pipe connecting part (EU1) of the evaporator (EU) and the lead-out pipe connecting part 21 of the particle number measuring unit (2) are arranged on a base body (9) so as to be orthogonal each other in a generally horizontal plane, and the secondary diluter (PND2) is arranged in a side in a horizontal direction so as to face the introducing pipe connecting part (EU1) of the evaporator (EU) and the lead-out pipe connecting part (21) of the particle number measuring unit (2). More specifically, the cylindrical space part side of the secondary diluter (PND2) is arranged to face the lead-out pipe connecting part (21) of the particle number measuring unit (2).

In the above-mentioned embodiment, the primary diluter has the function of collecting dusts, and a dust removing unit is not arranged upstream of the primary diluter, however, a dust removing unit may be arranged upstream of the primary diluter without providing the primary diluter with the function of collecting dust. With this arrangement, there is no need of arranging the internal space of the primary diluter along the vertical direction. In addition, the primary diluter and the secondary diluter have the identical structure, however, they may have different structure. In this case, the dust collecting part may be arranged for the primary diluter and the secondary diluter may not be provided with the dust collecting part. Furthermore, the diluter has a single introducing pipe to introduce both of the exhaust gas and the dilution gas into the internal space, however, the diluter may have an introducing pipe for exhaust gas that introduces the exhaust gas into the internal space and an introducing pipe for dilution gas that introduces the dilution gas into the internal space. In addition, the lead-out pipe of the primary diluter is of the curved pipe and the lead-out pipe of the secondary diluter is of the straight pipe in the above-mentioned embodiment, however, these lead-out pipes may be appropriately changed according to a layout of constituting members connected to downstream of the diluter. Furthermore, the introducing pipe of the diluter of the above-mentioned embodiment is arranged orthogonal to the center axis of the internal space and the lead-out pipe is arranged along the center axis of the internal space, however, the introducing pipe may be arranged along the center axis of the internal space and the lead-out pipe may be arranged orthogonal to the center axis of the internal space. In this case, in order to generate the swirling flow in the internal space, it is preferable to provide an agitating blade in the internal space.

Finally, the information processing unit will be explained in detail.

The system for determining the number of particles in accordance with this embodiment comprises an exhaust gas introduction port to introduce an exhaust gas of an engine, a dilution gas introduction port to introduce the dilution gas, a dilution unit to dilute the exhaust gas by mixing the dilution gas into the exhaust gas introduced into inside in a predetermined dilution factor, a particle number measuring unit that measures a number of solid particles in the exhaust gas diluted by the dilution unit, and an information processing unit that displays particle number information after dilution based on a measured result of the particle number measuring unit and particle number information prior to dilution obtained by the particle number information after dilution and the dilution factor of the dilution unit on a display in a switchable manner.

In accordance with this arrangement, it is possible to display not only the particle number information for the exhaust gas after dilution but also the particle number information for the exhaust gas prior to dilution, a process of calculating the particle number information of the exhaust gas prior to dilution by a user can be omitted, resulting in improving usability for the user. In addition, with the arrangement wherein the particle number information after dilution and the particle number information prior to dilution can be displayed in a switchable manner, there is no need of either making the window display complicated or making each space for displaying the information small. As a result, it is possible for the user to prevent misreading each of the particle number information so that usability of the system for determining the number of particles can be improved.

In case that the system for determining the number of particles further comprises an evaporator to vaporize volatile particles in the exhaust gas, there is a problem that particles contained in the exhaust gas attach to the pipe in the evaporator and its vicinity, especially in the pipe between the evaporator and the dilution unit due to, for example, the thermal phoresis phenomenon. Then, in order to display the particle number information with considering a particle loss because the particles attach to the pipe, it is preferable that the information processing unit displays particle number information after provided with loss correction obtained by a particle concentration reduction factor determined based on the particle number information after dilution, the dilution factor of the dilution unit and the particle number loss after the particles pass at least the evaporator in the dilution factor on the display in a switchable manner in addition to the particle number information after dilution and the particle number information prior to dilution. The particle concentration reduction factor is, for example, the PCRF (Particle Concentration Reduction Factor) determined by the ECE regulation. With this arrangement, it is possible not only to display the particle number information after dilution, the particle number information prior to dilution and the particle number information after loss correction, but also for the user to prevent misreading each particle number information and there is no need of making the display space small so that usability of the system for determining the number of particles can be improved.

In addition, it is preferable that the information processing unit shows a display for selection that is for a user to select a first window that can switch the particle number information after dilution and the particle number information prior to dilution and a second window that can switch the particle number information after dilution, the particle number information prior to dilution and the particle number information after the loss is compensated, and the window selected by the display for selection is shown on the display. With this arrangement, since the user can select the first window and the second window on purpose, it is easily possible to prevent mistakenly reading the particle number information shown on the window.

It is preferable that the information processing unit contains a selection check box as the display for selection and shows a window for dilution factor setting to set a dilution factor of the dilution unit, and in case that the user selects the second window for the particle number information, only the dilution factor whose particle concentration reduction factor is previously determined is selectively shown on the window for dilution factor setting. With this arrangement, in case of displaying the particle number information prior to dilution after correction of loss, it is possible to prevent from selecting a dilution factor whose particle concentration reduction factor has not been set so that the usability can be improved.

In order to further improve usability, it is preferable that the information processing unit shows the window for dilution factor setting for setting the dilution factor of the dilution unit, and either one of the first window where the particle number information after dilution and the particle number information prior to dilution are switchable and the second window where the particle number information after dilution, the particle number information prior to dilution and the particle number information after the loss is compensated are switchable is shown on the display based on the dilution factor input to the window for dilution factor setting.

Then, the information processing unit (4) of the system for determining the number of particles (100) of this embodiment shows the particle number information after dilution obtained from a measurement result of the particle number measuring unit (2), the particle number information prior to dilution obtained from the dilution factor of the dilution unit, and the particle number information after correction of loss obtained from the particle number information after dilution and the particle concentration reduction factor in a switchable manner on a display. In this embodiment, an example of a particle number concentration [number/cm$^3$] is shown as the particle number information. In addition, the particle number information prior to dilution is the information that is obtained by multiplying the particle number information after dilution and the dilution factor (concretely, a total dilution factor of the primary diluter (PND1) and the secondary diluter (PND2)) of the dilution unit. The particle number information after correction of loss is the information that is obtained by multiplying the particle number information after dilution and the particle concentration reduction factor. The particle concentration reduction factor is a coefficient determined based on the dilution factor of the dilution unit and the particle number loss after the particles pass at least the evaporator (EU) at this dilution factor. In other words, the particle concentration reduction factor is a coefficient combined by the dilution factor of the dilution unit and the particle number loss after the particles pass at least the evaporator (EU) at this dilution factor, and determined for each dilution factor. The particle concentration reduction factor is obtained from the particle loss at least near the evaporator (EU), however, since not only the particle loss due to the evaporator (EU) but also the particle loss due to a bending portion of the pipe is considered, the particle concentration reduction factor is determined with consideration of the particle loss in the pipe (including each device such as the evaporator (EU) or the like arranged in the pipe) connecting from the exhaust gas introducing port (PT1) to the particle number measuring unit (2) in this embodiment.

Figure 9:
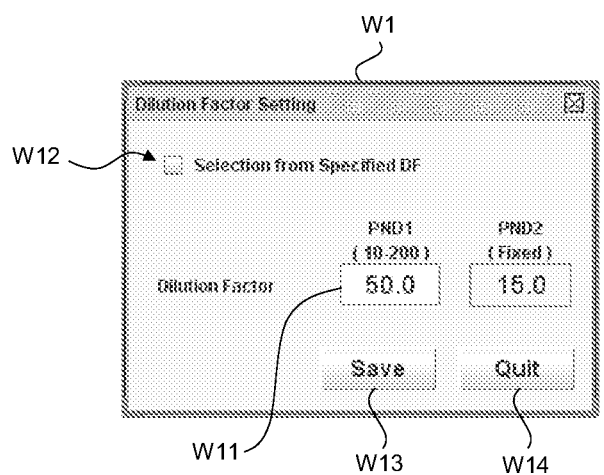
FIG. 9 is a window of dilution factor setting without using the particle concentration reduction factor.

Concretely, the information processing unit (4) displays a window for dilution factor setting (W1) shown in FIG. 9 on a display in setting the dilution factor prior to initiaton of selecting the particle number concentration of the exhaust gas. The window for dilution factor setting (W1) is a window for setting the dilution factor of the primary dilution unit (the primary diluter (PND1)) and the dilution factor of the secondary dilution unit (the secondary diluter (PND2)). In this embodiment, the dilution factor of the secondary diluter (PND2) is a fixed value (15 times in FIG. 9), and the window for dilution factor setting (W1) is a window to set the dilution factor of the primary diluter (PND1). The dilution factor of the primary diluter (PND1) can be arbitrarily set between 10 times~200 times by inputting a text into a dilution factor input box by a user. A code (W13) in FIG. 9 is a button to determine the dilution factor, and a code (W14) is a button to terminate the window.

Figure 10:
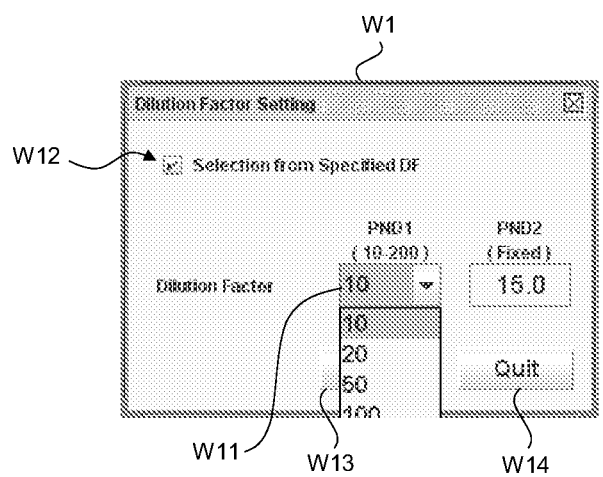
FIG. 10 is a window of dilution factor setting in case of using the particle concentration reduction factor.
Figure 11:
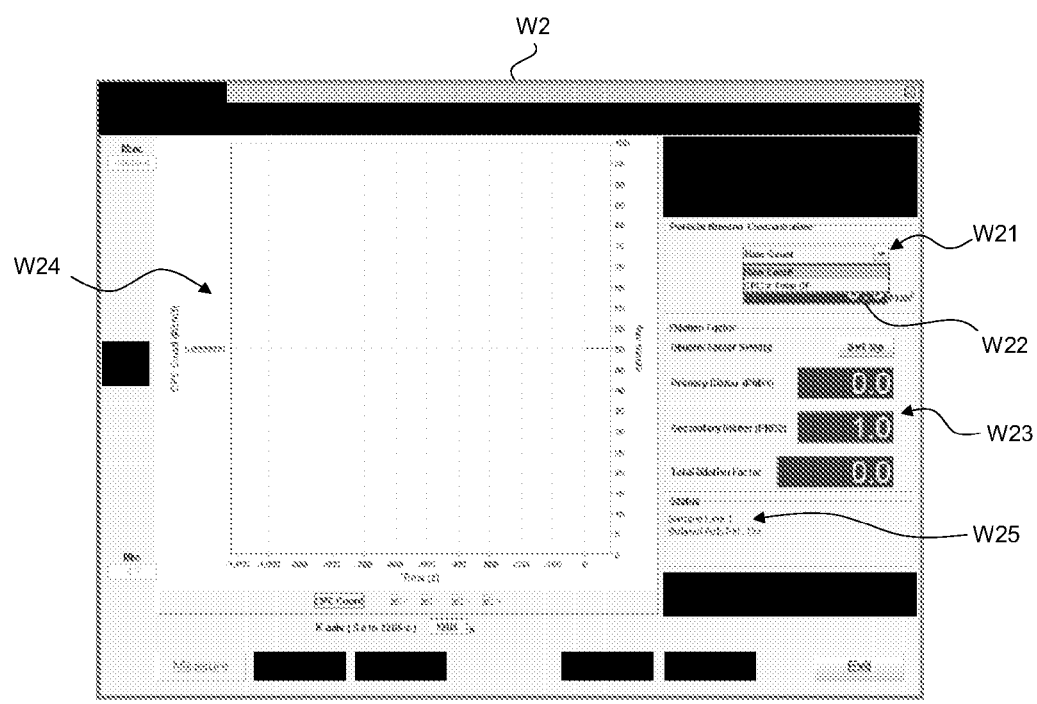
FIG. 11 is a window showing information on the number of particles without using the particle concentration reduction factor.
Figure 12:
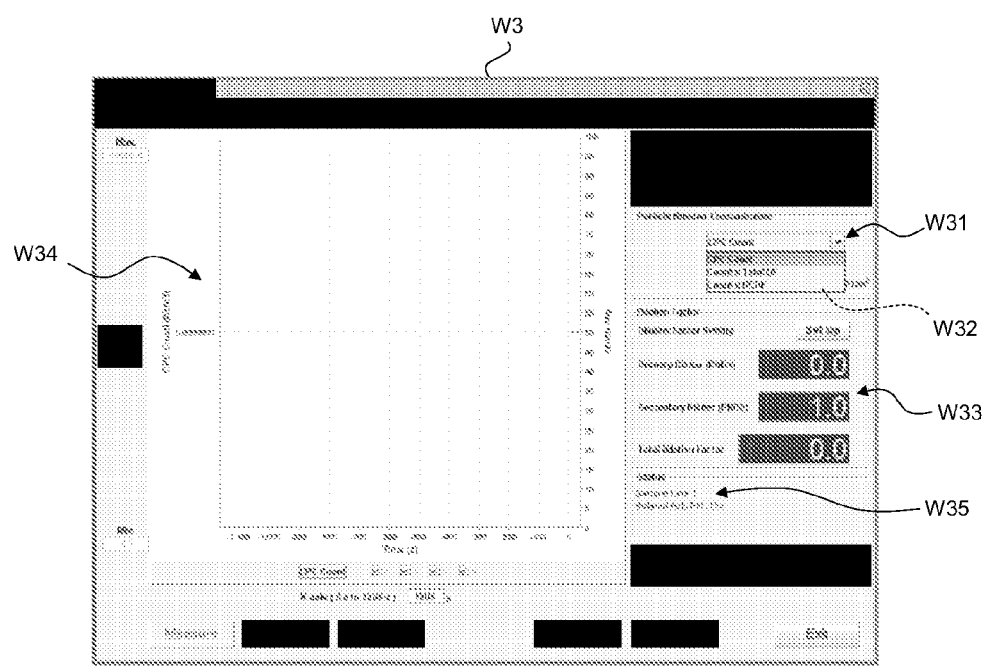
FIG. 12 is a window showing the information on the number of particles in case of using the particle concentration reduction factor.

On the window for dilution factor setting (W1) displayed is a selection check box (W12), concretely a display for selection for a user to select a first display window (W2) (refer to FIG. 11) or a second display window (W3) (refer to FIG. 12). In case that a user checks the selection check box (W12) by the use of the pointing device (refer to FIG. 10), the information processing unit (4) displays the second display window (W3) on the display. Meanwhile, in case that the user does not check the selection check box (W12), the information processing unit (4) displays the first display window (W2) on the display.

As shown in FIG. 11, the first display window (W2) is a display window that can switch the particle number concentration after dilution and the particle number concentration prior to dilution, and comprises a display switching part (W21) to switch the particle number concentration after dilution ("Raw Count" in FIG. 11) and the particle number concentration prior to dilution ("Count*Total DF" in FIG. 11), and a particle number information display area (W22) to display a particle number concentration selected in the display switching part (W21), for example, in real time. The display switching part (W21) makes it possible to select the particle number concentration after dilution (Raw Count) and the particle number concentration prior to dilution (Count*Total DF) by a pull-down menu when the user selects by the use of the pointing device. In addition, the first display window (W2) has a dilution factor display area (W23) to display the dilution factor of the dilution unit while counting the particle number and a time series data display area (W24) to show a time series change of the particle number concentration. Concretely, the dilution factor display area (W23) displays the dilution factor of the primary diluter (PND1), the dilution factor of the secondary diluter (PND2) and a total dilution factor of the primary diluter (PND1) and the secondary diluter (PND2). The first display window (W2) also has a status display area (W25) to display a sample line selected by a line selection mechanism (SCU).

In addition, as shown in FIG. 12, the second display window (W3) is a display window that can switch the particle number concentration after dilution, the particle number concentration prior to dilution and the particle number concentration after the loss is corrected, and comprises a display switching part (W31) to switch the particle number concentration after dilution ("CPC Count" in FIG. 12), the particle number concentration prior to dilution ("Count*Total DF" in FIG. 12) and the particle number concentration after the loss is corrected ("Count*PCRF" in FIG. 12), and a particle number information display area (W32) to display the particle number concentration selected by the display switching part (W31), for example, in real time. Other structure of the second display window (W3) is the same as that of the first display window (W2), and a code (W33) is the dilution factor display area, and a code (W34) is a time series data display area. The second display window (W3) also has a status display area (W35) that displays the sample line selected by the line selection mechanism (SCU). The particle number information display area (W32) in FIG. 12 is hidden by the pull-down menu of the display switching part (W31).

In addition, in case that the selection check box (W12) is checked in the window for dilution factor setting (W1), only the dilution factor whose particle concentration reduction factor is previously determined can be selected in the dilution factor input box (W11). Concretely, in case that the selection box (12) is checked, in order to make it possible to select only the dilution factor whose particle concentration reduction factor is previously determined, the information processing unit (4) displays the pull-down menu containing the dilution factors whose particle concentration reduction factor is previously determined in the dilution factor input box (W11). Then the dilution factor of the primary diluter (PND1) is set by selecting the dilution factor contained in the pull-down menu.

The dilution factor of the secondary diluter is the fixed value in the above-mentioned embodiment, however, the dilution factor of the secondary diluter may be arbitrarily set by a user similar to the primary diluter. In addition, the particle diameter in case of obtaining the particle concentration reduction factor is not limited to 30 nm, 50 nm and 100 nm, and may be other particle diameter. In the above embodiment, the particle concentration reduction factor is a mean value (arithmetical average) of the particle concentration reduction factor obtained for each particle diameter, however, a weighted mean value of the particle concentration reduction factor obtained for each particle diameter may be used as the mean particle concentration reduction factor. Furthermore, in the above-mentioned embodiment, the dilution factor of the primary diluter can be selected in the pull-down menu in case that the selection check box is checked, however, a text may be input as the dilution factor of the primary diluter. In this case, if the dilution factor whose particle concentration reduction factor is not set, it can be conceived that the dilution factor whose particle concentration reduction factor is set and that is the nearest to the input dilution factor is set. In addition, the window for dilution factor setting may not have the selection check box. In this case, the information processing unit may display the second display window on the display if the dilution factor input in the dilution factor input box is the dilution factor whose particle concentration reduction factor is previously set. With this arrangement, it is possible to simplify the operation of the user.

Effect of this Embodiment

In accordance with the system for determining the number of particles (100) having the above arrangement, since the dilution factor is calculated based on the dilution gas flow rate ($Q_1$) controlled by the dilution gas flow rate control part (MFC3) and a total flow rate ($Q_2+Q_3$) of the unit flow rate ($Q_2$) of the particle number measuring unit (2) and the set flow rate ($Q_3$) of the constant flow rate unit (CFO3) in the bypass flow channel (BL3), it is possible to omit a flow rate measuring mechanism that measures a flow rate of an exhaust gas flowing in a conventional secondary diluter (PND2). As a result, it is possible to simplify and downsize the system configuration, and to decrease its cost as well. In addition, a suction pump conventionally that is provided for the flow channel (ML) where the particle number measuring unit (2) is arranged and for the bypass flow channel (BL) respectively can be commonly used, it is possible to simplify and downsize the configuration of the system, and to reduce its cost.

This invention is not limited to the above-mentioned embodiment.

For example, the above-mentioned embodiment assumes a case that the temperature of the constant flow unit (CFO) arranged inside of the particle number measuring unit (2) is not adjusted, and the unit flow rate of the particle number measuring unit (2) is corrected by the use of the pressure and the temperature near the upstream of the particle number measuring unit (2). Meanwhile, in case that the temperature of the constant flow rate unit (CFO) arranged inside of the particle number measuring unit (2) is adjusted, the unit flow rate of the particle number measuring unit (2) is collected by the use of the pressure near the upstream of the particle number measuring unit (2), and there is no need of correcting the unit flow rate by the use of the temperature near the upstream of the particle number measuring unit (2).

In addition, in the above-mentioned embodiment, the pressure sensor (P1) and the temperature sensor (T1) are arranged near the upstream of the constant flow rate unit (CFO3) in the third bypass flow channel (BL3) and the pressure sensor (P1) and the temperature sensor (T1) are arranged near the upstream of the particle number measuring unit (2) in the main flow channel (ML), however, the pressure sensor (P1) and the temperature sensor (T1) may be shared. Concretely, the commonly used pressure sensor and the temperature sensor may be arranged near the upstream of a bifurcating point of the main flow channel (ML) and the third bypass flow channel (BL3).

In addition, it is a matter of course that the present claimed invention is not limited to the above-mentioned embodiment and may be variously modified without departing from a spirit of the invention.

POSSIBLE APPLICATIONS IN INDUSTRY

In accordance with this invention, it is possible to simplify and downsize the configuration of the system for determining the number of particles, and to reduce its cost as well.

The invention claimed is:

1. A system for determining a number of particles comprising an exhaust gas introduction port to introduce an exhaust gas of an engine, a dilution gas introduction port to introduce a dilution gas, a main flow channel whose one end is connected to the exhaust gas introduction port, a dilution gas flow channel whose one end is connected to the dilution gas introduction port and whose other end is connected to the main flow channel, a secondary diluter arranged at a connecting point of the main flow channel and the dilution gas flow channel or downstream of the connecting point, a primary diluter arranged upstream of the connecting point on the main flow channel such that a flow rate measuring device is not arranged between the secondary diluter and the primary diluter, and that dilutes the exhaust gas of the engine, a dilution gas flow rate control part arranged in the dilution gas flow channel and that controls a flow rate of the dilution gas introduced into the secondary diluter, a particle number measuring unit, having a function of a constant flow rate, arranged downstream of the secondary diluter through a valve and that measures a number of solid particles in the diluted exhaust gas, a bypass flow channel that bifurcates from between the secondary diluter and the particle number measuring unit in the main flow channel and in which a constant flow rate unit and a valve are arranged, a suction pump connected downstream of a converging point of the main flow channel and the bypass flow channel in order to introduce the exhaust gas into the main flow channel and the bypass flow channel, and an information processing unit that receives the dilution gas flow rate controlled by the dilution gas flow rate control part and a unit flow rate as being a flow rate flowing in the particle number measuring unit and a set flow rate of the constant flow rate unit in the bypass flow channel, and calculates a dilution factor of the exhaust gas based on the dilution gas flow rate and a total of the unit flow rate and the set flow rate.

2. The system for determining a number of particles described in claim 1, wherein the information processing unit corrects the set flow rate of the constant flow rate unit in the bypass flow channel by closing the valve arranged upstream of the particle number measuring unit and opening the valve arranged in the bypass flow channel so as to flow a flow rate controlled by the dilution gas flow rate control part into the bypass flow channel.

3. The system for determining a number of particles described in claim 2, wherein the information processing unit corrects the set flow rate of the constant flow rate unit in the bypass flow channel by making use of a temperature and a pressure upstream of the constant flow rate unit at a time of correcting the constant flow rate unit in the bypass flow channel and a temperature and a pressure upstream of the constant flow rate unit in the bypass flow channel at a time of measuring the number of the particles as a parameter.

4. The system for determining a number of particles described in claim 2, wherein the information processing unit corrects the unit flow rate of the particle number measuring unit by making use of a pressure upstream of the particle number measuring unit at a time of correcting the unit flow rate of the particle number measuring unit and a pressure upstream of the particle number measuring unit at a time of measuring the number of the particles as a parameter.

5. The system for determining a number of particles described in claim 1, wherein the information processing unit corrects the unit flow rate of the particle number measuring unit in the bypass flow channel by closing the valve arranged in the bypass flow channel and opening the valve arranged upstream of the particle number measuring unit so as to flow a flow rate controlled by the dilution gas flow rate control part into the main flow channel.

* * * * *